(12) United States Patent
Gericke et al.

(10) Patent No.: US 6,737,426 B1
(45) Date of Patent: May 18, 2004

(54) SULFONYLOXAZOLEAMINES

(75) Inventors: Rolf Gericke, Seeheim (DE); Henning Böttcher, Darmstadt (DE); Michael Gassen, Griesheim (DE); Hartmut Greiner, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/148,078

(22) PCT Filed: Nov. 24, 2000

(86) PCT No.: PCT/EP00/11734

§ 371 (c)(1),
(2), (4) Date: May 28, 2002

(87) PCT Pub. No.: WO01/38316

PCT Pub. Date: May 31, 2001

(30) Foreign Application Priority Data

Nov. 25, 1999 (DE) .......................... 199 56 791

(51) Int. Cl.[7] .................. A61K 31/496; C07D 403/12; C07D 413/04; A61P 25/00

(52) U.S. Cl. .................. 514/252.13; 514/253.01; 514/254.02; 514/340; 544/359; 544/360; 544/367; 546/271.4

(58) Field of Search .................. 514/252.13, 253.01, 514/254.02, 340, 377; 544/359, 360, 367; 546/271.4; 548/215, 225, 232, 233, 235

(56) References Cited

U.S. PATENT DOCUMENTS

| 5,990,105 A | 11/1999 | Bös et al. |
| 6,194,410 B1 | 2/2001 | Bös et al. |
| 6,441,013 B1 * | 8/2002 | Greiner et al. ............... 514/376 |

FOREIGN PATENT DOCUMENTS

| EP | 0 930 302 A | 7/1999 |
| EP | 0930302 A2 * | 7/1999 |
| EP | 0 941 994 A | 9/1999 |
| WO | WO 00 37452 A | 6/2000 |

OTHER PUBLICATIONS

Database Chemabs 'Online! Chemical Abstracts Service, Colombus, Ohio, US; Database accession No. 2001:163527 CHEMCATS, XP002166640,Piperidine, 1–'2–(2–furanyl)–4–' (4–methylphenyl) sulfonyll –5–oxazolyll –(RN 313958–86–0 & Pharma Library Collection, Sep. 18, 2000.
Database Chemabs 'Online! Chemical Abstracts Service, Columbus, Ohio, US; Database accession No. 2001:79063 CHEMCATS, XP002166641, 5–Oxazolamine, 2–(2–furanyl)–4–' (4–methyllphenyl) sulfonyll –N–(phenylmethyl)–(RN 304658–14–8) & Heterocyclic Compounds Catalog, Mar. 21, 2000.

Database Chemabs 'Online! Chemical Abstracts Service, Colombus, Ohio, US; Database accession No. 2001:79059 CHEMCATS, XP002166642 ,2–Furancarboxamide, N–'2, 2–dichioro–1–' (4–methylphenyl) sulfonyll ethyenyll–(RN 304658–10–4) & Heterocyclic Compounds Catalog, Mar. 21, 2000.
Database Chemabs 'Online! Chemical Abstracts Service, Colombus, Ohio, US; Database accession No. 2000:994186 CHEMCATS, XP002166643, Piperidine, 1–'2–(2–furanyl)–4–(phenylsulfonyl)–5–oxazolyll–(RN 303753–71–1) & Heterocyclic Compounds Catalog, Mar. 21, 2000.

(List continued on next page.)

*Primary Examiner*—Rita Desai
*Assistant Examiner*—Robert Shiao
(74) *Attorney, Agent, or Firm*—Millen, White, Zelano & Branigan, P.C.

(57) ABSTRACT

The invention relates to compounds of the general formula (I)

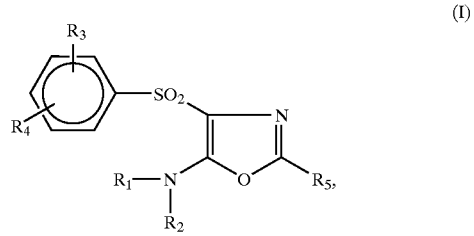

where $R_1$ and $R_2$ independently of one another are H, —$R_6$, $C_3$–$C_8$-cycloalkyl, —$(CH_2)_n$—$R_7$, —$(CH_2)_n$—O—$R_6$, —$(CH_2)_n$—$NH_2$, —$(CH_2)_n$—$NHR_6$, —$(CH_2)$—$N(R_6)_2$, $C_2$–$C_6$-alkenyl or, where appropriate, together form a mononuclear saturated heterocycle having one or two nitrogen, oxygen and/or sulfur atoms, $R_3$ and $R_4$ independently of one another are H, —$R_6$, —$CF_3$, —$NO_2$, —Hal, —OH, —O—$R_6$, —$NH_2$, —NH—$R_6$ or —$N(R_6)_2$, $R_5$ is a 5- or 6-membered, saturated or unsaturated heterocycle having one or two nitrogen, oxygen and/or sulfur atoms which may be mono- or disubstituted by $R_6$, —$CF_3$, —$NO_2$, —Hal, —OH, —O—$R_6$, —$NH_2$, —NH—$R_6$ or —$N(R_6)_2$, and $R_6$ is $C_1$–$C_6$-alkyl, $R_7$ is $R_3$- and/or $R_4$-substituted phenyl, n is 0 to 2, and physiologically acceptable salts or solvates thereof.

The invention also relates to the use of the compounds of the general formula I as medicaments.

10 Claims, No Drawings

OTHER PUBLICATIONS

Database Chemabs 'Online! Chemical Abstracts Service, Colombus, Ohio, US; Database accession No. 2000:993038 CHEMCATS, XP002166644 Morpholine, 4-'2-(2-furanyl)-4-(phenylsulfonyl)-5-oxazolyll-(RN 303753-70-0) & Heterocyclic Compounds Catalog, Mar. 21, 2000.

Database Chemabs 'Online! Chemical Abstracts Service, Colombus, Ohio, US; Database accession No. 2000:993036 CHEMCATS, XP002166645 Morpholine, 4-'4-' (4-chlorophenyl) sulfonyll-2-(2-furanyl)-5-oxazolyll-(RN 303753-68-6) & Heterocyclic Compounds Catalog, Mar. 21, 2000.

Database Chemabs 'Online! Chemical Abstracts Service, Colombus, Ohio, US; Database accession No. 2000:993035 CHEMCATS, XP002166646 Piperidine, 1-'4-' (4-chlorophenyl) sulfonyll-2-(2-furanyl)-5-oxazolyll-(RN 303753-67-5) & Heterocyclic Compounds Catalog, Mar. 21, 2000.

Database Chemabs 'Online! Chemical Abstracts Service, Colombus, Ohio, US; Database accession No. 2000:993034 CHEMCATS, XP002166647 5-Oxazolamine, 4-'(4-chlorophenyl) sulfonyll-2-(2-furanyl)-N-(phenylmethyl)-(RN 303753-66-4) & Heterocyclic Compounds Catalog, Mar. 21, 2000.

Database Chemabs 'Online! Chemical Abstracts Service, Colombus, Ohio, US; Database accession No. 2000:993033 CHEMCATS, XP002166648 Morpholine, 4-'2-(2-furanyl)-4-'(4-methylphenyl) sulfonyll-5-oxazolyll-(RN 303753-65-3) & Heterocyclic Compounds Catalog, Mar. 21, 2000.

* cited by examiner

SULFONYLOXAZOLEAMINES

The invention relates to sulfonyloxazolamines of the general formula I and to their use as medicaments, and to a process for their preparation, to the intermediates employed in the preparation process and to a process for preparing the intermediates.

The sulfonyloxazolamines according to the invention are compounds of the general formula (I)

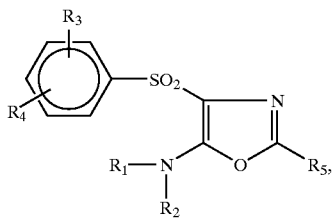

(I)

where

R$_1$ and R$_2$ independently of one another are H, —R$_6$, —C$_3$–C$_8$-cycloalkyl, —(CH$_2$)$_n$—R$_7$, —(CH$_2$)$_n$—O—R$_6$, —(CH$_2$)$_n$—NH$_2$, —(CH$_2$)$_n$—NHR$_6$, —(CH$_2$)—N(R$_6$)$_2$, C$_2$–C$_6$-alkenyl or, where appropriate, together form a mononuclear saturated heterocycle having one or two nitrogen, oxygen and/or sulfur atoms, R$_3$ and R$_4$ independently of one another are H, —R$_6$, —CF$_3$, —NO$_2$, —Hal, —OH, —O—R$_6$, —NH$_2$, —NH—R$_6$ or —N(R$_6$)$_2$, R$_5$ is a 5- or 6-membered, saturated or unsaturated heterocycle having one or two nitrogen, oxygen and/or sulfur atoms which may be mono- or disubstituted by —R$_6$, —CF$_3$, —NO$_2$, —Hal, —OH, —O—R$_6$, —NH$_2$, —NH—R$_6$ or —N(R$_6$)$_2$, and R$_6$ is C$_1$–C$_6$-alkyl, R$_7$ is R$_3$- and/or R$_4$-substituted phenyl, n is 0 to 2, and physiologically acceptable salts or solvates thereof.

Some sulfonyloxazolamines are known from various earlier publications: V. A. Chervonyi et al., *Ukr. Khim. Zh.* (Russian Ed.) 1991, 57(4), 415–418 or V. A. Chervonyi et al., *Zh. Org. Khirm.* 1988, 24(2), 453–4 corresponding to V. A. Chervonyi et al., *J. Org. Chem. USSR* (Engl. transl.) 1988, 24, 401. The latter publication describes, for example, the preparation of 4-tolylsulfonyl-5-dimethylamino-2-phenyl-1,3-oxazole.

The invention was based on the object of finding sulfonyloxazolamines with valuable properties. In particular it was important to find pharmacologically active sulfonyloxazolamines.

The object is achieved by compounds of the general formula I described hereinbefore and physiologically acceptable salts or solvates thereof.

It was found that the compounds of the formula I and their pharmacologically active salts surprisingly have a selective affinity to 5-HT6 receptors, together with good tolerability, and they are therefore 5-HT6 receptor ligands. They exhibit 5-HT6-antagonistic or 5-HT6-agonistic actions.

5-HT6 receptors form a subfamily of 5-HT receptors. The neurotransmitter 5-hydroxytryptamine (5-HT), also known as serotonin, is an important regulating neurotransmitter in the brain, whose actions are assisted by a family of receptors which, at the current level of knowledge, contains 13 G protein-coupled receptors and an ion channel. The group of G protein-coupled receptors also includes the 5-HTG receptors. Some representatives have been cloned and to some extent histologically and biochemically investigated (see, for example, Kohen et al. (1996) *J. Neurochem* 66, 47–56; Ruart et al. (1993), 193, 268–76).

The greatest density of the serotonin 5-HT6 receptors in the brain is found in the olfactory tubercle, in the nucleus accumbens, in the striatum, in the dentate gyrus and in the CA1-3 regions of the hippocampus. These regions are involved to a particular extent in psychiatric disorders such as, for example, schizophrenia or depression. Moreover, it is known from animal experiments that the administration of 5-HT6 antisense oligonucleotides causes a behavioural syndrome which corresponds to that of dopamine agonists. Furthermore, hyperactivity of the dopaminergic neurotransmitter system in schizophrenia (dopamine hypothesis of schizophrenia) is pathophysiologically confirmed. However, dysfunctions of the dopamine system in various forms of depression have been demonstrated. Of the established or alternatively newer therapeutics which are employed in clinical practice for the treatment of these psychiatric disorders, a large number moreover bind to the 5-HT6 receptor. The atypical neuroleptics (e.g. clozapine) and the tricyclic antidepressants (e.g. amitriptyline) may be mentioned here in particular.

Moreover, it was found in animal experimental investigations that 5-HT6 receptors in the brain control cholinergic neurotransmission. Cholinergics are employed in disorders with memory disturbances such as, for example, Alzheimer's disease.

For these reasons, it can be concluded that there is an involvement of the 5-HT6 receptor in psychiatric and neurological disorders such as, especially, schizophrenia, depression and Alzheimer's.

The compounds of the formula I and their physiologically acceptable salts are therefore suitable as therapeutic active compounds for disorders of the central nervous system. The compounds of the formula I and physiologically acceptable salts or solvates thereof are particularly suitable for the treatment of psychoses, schizophrenia, manic depression (B. L. Roth et al., *J. Pharmacol. Exp. Ther.* 1994, 268, 1403–1410), depression (D. R. Sibley et al., *Mol. Pharmacol.* 1993, 43, 320–327), neurological disorders (A. Bourson et al., *J. Pharmacol. Exp. Ther.* 1995, 274, 173–180), memory disorders, Parkinson's disease, amyotrophic lateral sclerosis, Alzheimer's disease, Huntington's disease (A. J. Sleight et al., *Neurotransmitters* 1995, 11, 1–5), bulimia, anorexia nervosa or other eating disorders, compulsive acts or of premenstrual syndrome. Solvates of the compounds of the formula I are understood as meaning adducts of "inert" solvent molecules to the compounds of the formula I, which are formed on account of their mutual force of attraction. Solvates are, for example, mono- or dehydrates or alcoholates.

For all radicals which occur one or more times it holds true that their meanings are independent of one another.

R$_3$ and R$_4$ are preferably and independently of one another methyl, methoxy, chlorine and bromine or hydrogen.

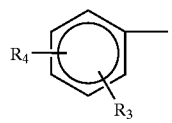

is preferably phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-N,N-dimethylaminophenyl, o-, m- or p-nitrophenyl, o-, m- or p-hydroxyphenyl, o-, m- or p-methoxyphenyl, o-, m- or p-ethoxyphenyl, o-, m-, p-trifluoromethylphenyl, o-, m- or p-fluorophenyl, o-, m- or p-chlorophenyl, o-, m- or p-bromophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl.

Particularly preferred for

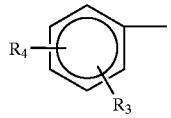

is phenyl, o- or p-methylphenyl, o- or p-chlorophenyl, p-bromophenyl, p-methoxyphenyl or 2,4-dichlorophenyl.

—Hal is fluorine, chlorine or bromine.

$R^1$ and $R^2$ together may also form a mononuclear saturated heterocycle having from 1 to 2 N, O and/or S atoms.

This heterocycle is preferably tetrahydro-2- or -3-furyl, 1,3-dioxolan-4-yl, tetrahydro-2- or -3-thienyl, 1-, 2- or 3-pyrrolidinyl, tetrahydro-1-, -2- or 4-imidazolyl, tetrahydro-1-, -3- or 4-pyrazolyl, 1-, 2-, 3- or 4-piperidinyl, 1-, 2-, 3- or 4-perhydroazepinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl or 1-, 2- or 3-piperazinyl, 1-Piperidinyl or 4-morpholinyl is particularly preferred.

Compounds in which $R_1$ is H are preferred.

Furthermore, compounds of the general formula I in which $R_2$ is $R_6$ are preferred.

Moreover, $R_3$ and/or $R_4$ are preferably H.

$R_5$ is preferably 2-furyl, 2-thienyl or 3- or 4-pyridyl.

$R_6$ is linear or branched, and has 1 to 6, preferably 1, 2, 3 or 4, C atoms. $R_6$ is preferably methyl, furthermore ethyl, propyl, butyl, isobutyl, sec-butyl or tert-butyl, in addition also pentyl, 1-, 2- or 3-methylbutyl, 1,1-, 1,2- or 2,2-dimethylpropyl, 1-ethylpropyl or hexyl.

Methyl is particularly preferred.

Alkenyl is preferably allyl, 2- or 3-butenyl, isobutenyl, sec-butenyl, in addition is preferably 4-pentenyl, isopentenyl or 5-hexenyl. Allyl is particularly preferred for alkenyl.

A base of the general formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, p-toluenesulfonic acid, naphthalenemono- and disulfonic acids or lauryl sulfuric acid. Salts with physiologically unacceptable acids, e.g. picrates, can be used for the isolation and/or purification of the compounds of the formula I.

The invention further relates to the use of the compounds according to the general formula I and physiologically acceptable salts and solvates thereof for preparing medicaments, in particular for preparing anticonvulsants, nootropics, anti-inflammatories, neuroprotectants and cerebroprotectants and for preparing medicaments for the treatment of diseases of the central nervous system, in particular for the treatment of schizophrenia, depression, pathological anxiety states, epilepsy, pathological memory disorders such as Alzheimer's disease, neurological disorders, amyotrophic lateral scleroses, Huntington's disease, disorders of the gastrointestinal tract, functional gastropathy, irritable bowel syndrome, bulimia, anorexia nervosa, compulsive acts (obsessive-compulsive disorder, OCD), premenstrual syndrome, migraine, drug addictions, sleeping disorders and/or for the treatment of head and spinal injuries.

The substances according to the invention are as a rule administered here in a dose of preferably between approximately 1 and 500 mg, in particular between 5 and 100 mg, per dose unit. The daily dose is preferably between approximately 0.02 and 10 mg/kg of body weight. The specific dose for each patient, however, depends on all sorts of factors, for example on the efficacy of the specific compound employed, on the age, body weight, general state of health, and sex, on the diet, on the time and route of administration, and on the excretion rate, pharmaceutical combination and severity of the particular disorder to which the therapy applies. Oral administration is preferred.

The compounds of the general formula I may also be employed as pesticides.

The invention further relates to a pharmaceutical preparation comprising at least one compound according to the general formula I and physiologically acceptable salts and solvates thereof and, where appropriate, vehicles and/or excipients.

These preparations can be used as pharmaceuticals in human or veterinary medicine.

Possible vehicles are organic or inorganic substances which are suitable for enteral (e.g. oral), or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc or petroleum jelly. Tablets, pills, coated tablets, capsules, powders, granules, syrups, juices or drops, in particular, are used for oral administration, suppositories are used for rectal administration, solutions, preferably oily or aqueous solutions, in addition suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain excipients such as lubricants, preservatives, stabilizers and/or wetting agents, emulsifiers, salts for affecting the osmotic pressure, buffer substances, colourants, flavourings and/or one or more other active compounds, e.g. one or more vitamins.

For the subject of the invention, of the therapeutic active compounds of the formula I or their physiologically acceptable salts or solvates, of the use of the compounds of the formula I or their physiologically acceptable salts or solvates as therapeutic active compounds or of the production of a pharmaceutical preparation for the treatment of disorders of the central nervous system, all the more preferred are compounds of the formula I, the more radicals have one of the preferred or particularly preferred meanings mentioned hereinbefore.

The invention further relates to the preparation of compounds of the general formula I, where $R_1R_2NH$ is reacted with compounds of the general formula II or III.

The invention also relates to the compounds of the general formula II:

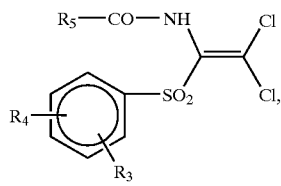

(II)

where $R_3$ and $R_4$ independently of one another are H, —$R_6$, —$CF_3$, —$NO_2$, —Hal, —OH, —O—$R_6$, —$NH_2$, —NH—$R_6$ or —$N(R_6)_2$, $R_5$ is a 5- or 6-membered, saturated or unsaturated heterocycle having one or two nitrogen, oxygen and/or sulfur atoms which may be mono- or disubstituted by $R_6$, —$CF_3$, —$NO_2$, —Hal, —OH, —O—$R_6$—$NH_2$, —NH—$R_6$ or —$N(R_6)_2$, and $R_6$ is $C_1$–$C_6$-alkyl.

The invention also relates to the compounds of the general formula III

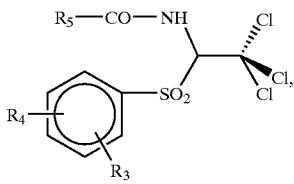

(III)

where $R_3$ and $R_4$ independently of one another are H, —$R_6$, —$CF_3$, —$NO_2$, —Hal, —OH, —O—$R_6$, —$NH_2$, —NH—$R_6$ or —$N(R_6)_2$, $R_5$ is a 5- or 6-membered, saturated or unsaturated heterocycle having one or two nitrogen, oxygen and/or sulfur atoms which may be mono- or disubstituted by $R_6$, —$CF_3$, —$NO_2$, —Hal, —OH, —O—$R_6$, —$NH_2$, —NH—$R_6$ or —$N(R_6)_2$, and $R_6$ is $C_1$–$C_6$-alkyl.

The compounds of the general formula I may be synthesized according to the following synthesis scheme (referring to V. A. Chervonyi et al., *Ukr. Khim. Zh.* (Russ. Ed.) 1991, 57(4), 415–418; V. A. Chervonyi et al., *Zh. Org. Khim.* 1988, 24(2), 453–4 corresponding to V. A. Chervonyi et al., *J. Org. Chem. USSR* (Engl. transl.) 1988, 24, 401; F. Weygand et al. *Chem. Ber.* 1966, 99, 1944–1956; H. Böhrme et al. *Arch Pharmaz.*, 1961, 294, 307–311; A. N. Meldrum and G. M. Vad *J. Indian Chem. Soc.* 1936, 13, 117–118; D. Z. Barczynski and Z. Eckstein *Przem Chem.*, 1978, 57, 176–177; F. Kasper and H. Böttiger *Z. Chem.* 1987, 27, 710–71):

Synthesis scheme

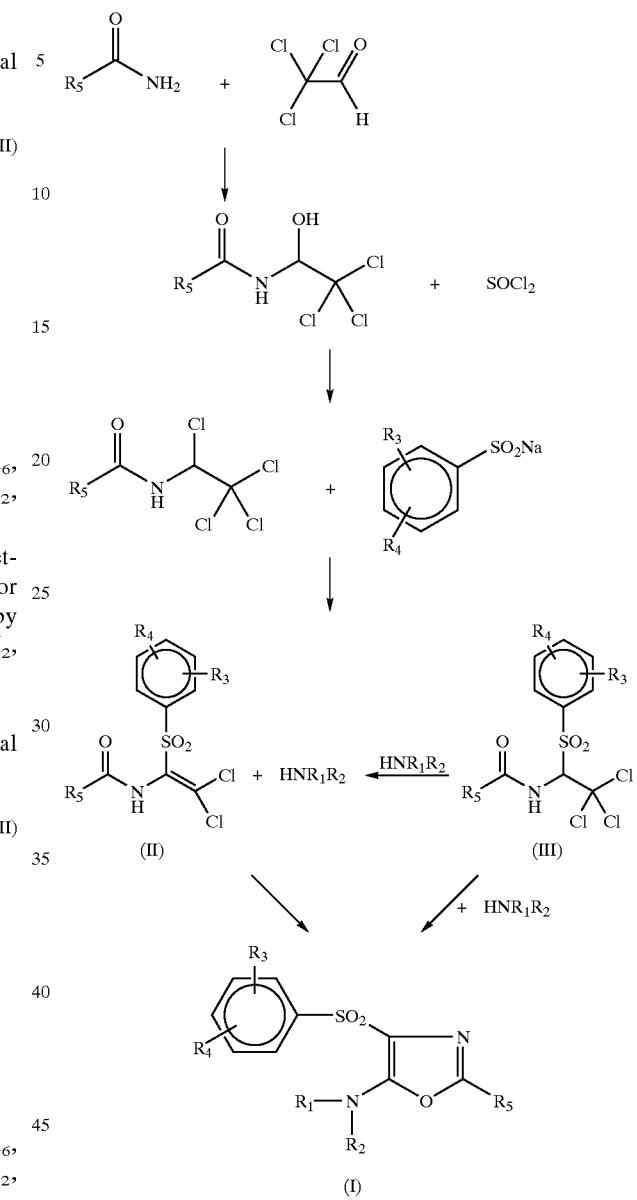

In the synthesis scheme shown beforehand, an amide of the formula $R_5CONH_2$ is reacted with chloral resulting in the corresponding "aldehyde ammonia". This is reacted with thionyl chloride resulting in the corresponding tetrachloroethyl derivative. This is subsequently reacted with substituted or unsubstituted sodium benzenesulfinate. This results in a compound of the general formula II or III. Both the compounds of the formula II and the compounds of the formula III react with an amine of the formula $R_1R_2NH$ with cyclization to give sulfonyloxazolamines of the general formula I.

The suitable reaction conditions of the reactions mentioned from the synthesis scheme are known from the references V. A. Chervonyi et al., *Ukr. Khim. Zh.* (Russ. Ed.) 1991, 57(4), 415–418 or V. A. Chervonyi et al., *Zh. Org. Khim.* 1988, 24(2), 453–4 corresponding to V. A. Chervonyi et al., *J. Org. Chem. USSR* (Engl. transl.) 1988, 24, 401, or from standard works such as, for example, Houben-Weyl, Methoden der organischen Chemie [Methods of Organic Chemistry], Georg-Thieme-Verlag, Stuttgart. In this case, use can also be made of variants which are known per se, but not mentioned here in greater detail.

The invention also relates to a process for preparing a compound according to the general formula (II), where a) $R_5$—$CONH_2$ is added to chloral,
b) the product from a) is chlorinated with thionyl chloride,
c) the product from b) is reacted with an alkali metal salt of a compound of the general formula (IV)

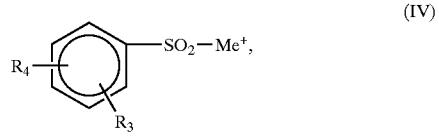

(IV)

where $R_3$ and $R_4$ have the meanings listed hereinbefore and $Me^+$ is an alkali metal cation, preferably $Na^+$.

EXAMPLE 1

Preparation of (4-phenylsulfonyl-2-pyridin-3-yl-oxazol-5-yl)methylamine

N-(1-Phenylsulfonyl-2,2-dichlorovinyl)nicotinamide (0.4 g, 1.120 mmol) is dissolved in tetrahydrofuran, mixed with methylamine (2.607 ml, 2M in tetrahydrofuran, 4.480 mmol) and stirred overnight at room temperature. The resulting precipitate was filtered off with suction and discarded, the mother liquor was concentrated in a rotary evaporator and the residue was crystallized using a small amount of isopropanol, filtered off with suction and dried in air.

m.p.: 191–193° C., decomposition.

EXAMPLE 2

Preparation of (4-phenylsulfonyl-2-thiophen-2-yl-oxazol-5-yl)benzylamine

N(1-Phenylsulfonyl-2,2,2-trichloroethyl)thiophene-2-carboxamide (0.4 g, 1.003 mmol) is dissolved in tetrahydrofuran, mixed with benzylamine (0.428 g, 4.012 mmol) and stirred overnight at room temperature. The resulting precipitate was filtered off with suction and discarded, the mother liquor was concentrated in a rotary evaporator and the residue was crystallized in 15 ml of petroleum ether, filtered off with suction and dried in air.

m.p.: 137–139° C.

EXAMPLE 3

Preparation of 1-(4-phenylsulfonyl-2-o-tolyl-oxazol-5-yl)piperazine hydrochloride 1-(4-Phenylsulfonyl-2-o-tolyl-oxazol-5-yl)piperazine (0.2 g, 0.556 mmol) was dissolved in tetrahydrofuran (15 ml) and methanol (15 ml), mixed with methanolic hydrochloric acid (2 ml) at room temperature and subsequently stirred for 1 h. The precipitated crystals were filtered off with suction, washed with a small amount of tetrahydrofuran and dried in air.

m.p.: 239–240° C., decomposition.

EXAMPLES 4–40

The following compounds were prepared analogously.
Abbreviations:
Me: methyl
Et: ethyl
Ph: phenyl
dec.: decomposition

| Example | $R_1$ | $R_2$ | $R_3$ | $R_5$ | M.p. [° C.] |
|---|---|---|---|---|---|
| 4 | Me | H | Ph | 2-furyl | 151–158 (dec.) |
| 5 | —(CH$_2$)$_3$—OMe | H | Ph | 2-furyl | 110–111 |
| 6 | cyclopropyl | H | Ph | 2-furyl | 123–124 |
| 7 | Ph | H | Ph | 2-furyl | 157–158 (dec.) |
| 8 | —CH$_2$—(2-OMe-phenyl) | H | Ph | 2-furyl | 129–132 |

-continued
| Example | R₁ | R₂ | R₃ | R₅ | M.p. [° C.] |
|---|---|---|---|---|---|
| 9 | Me | H | 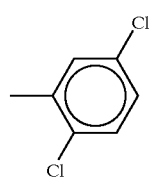 | 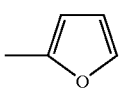 | 155–157 |
| 10 | —CH₂Ph | H | 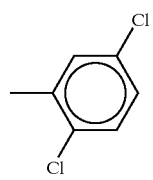 | 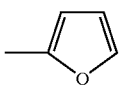 | 174–175 |
| 11 | Me | H | Ph | 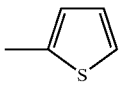 | 183° C. (dec.) |
| 12 | —CH₂Ph | H | Ph | 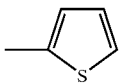 | (124) 137–139 |
| 13 | Me | H | Ph | 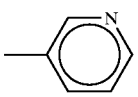 | 191–193 (dec.) |
| 14 | —CH₂Ph | H | Ph | 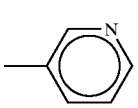 | 182–183 |
| 15 | 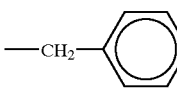 | H | Ph | 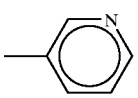 | 175.5–180.5 |
| 16 | Et | H | 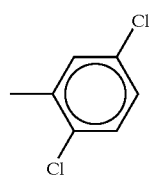 | 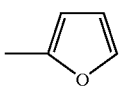 | 146.5–147.5 |
| 17 | Et | H | Ph | 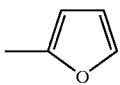 | 153–153.5 |
| 18 | Me | H | 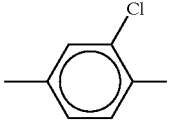 | 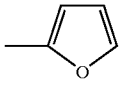 | 167–168 |
| 19 | Me | H |  | 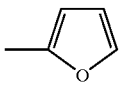 | 184 (dec.) |

-continued
| Example | R₁ | R₂ | R₃/R₄ | R₅ | M.p. [° C.] |
|---|---|---|---|---|---|
| 20 | Et | H | 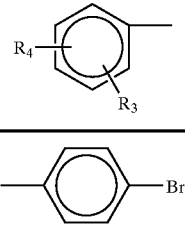 4-Br-C₆H₄ | 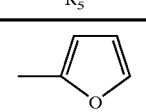 2-furyl | 181 (dec.) |
| 30 | 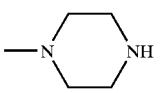 N-methylpiperazinyl | | Ph | 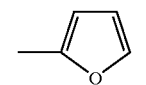 2-furyl | 130–131 |
| 30 (HCl salt) | 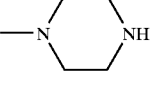 N-methylpiperazinyl | | Ph | 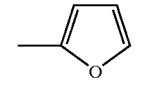 2-furyl | 239–240 (dec.) |
| 31 | Et | H | Ph | 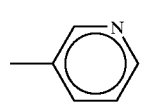 pyridyl | 179.5–180.5 |
| 32 | Me | H | Ph | 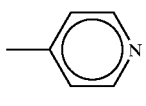 pyridyl | 225 (dec.) |
| 33 | Et | H | Ph | 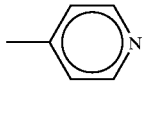 pyridyl | 200–201 |
| 34 | Me | H | Ph | 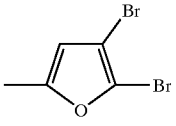 3,4-dibromofuryl | 207 (dec.) |
| 35 | Me | H | 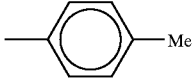 4-Me-C₆H₄ | 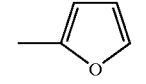 2-furyl | 165–166 |
| 36 | Et | H | 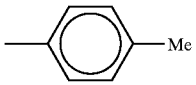 4-Me-C₆H₄ | 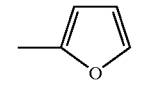 2-furyl | 172.5–173.5 |
| 37 | Me | H | 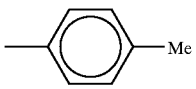 4-Me-C₆H₄ | 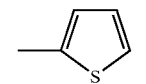 2-thienyl | 183–184 (dec.) |
| 38 | Me | H | Ph | 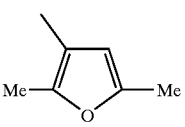 2,5-dimethyl-3-methylfuryl | 164–165 (dec.) |
| 39 | Et | H | Ph | 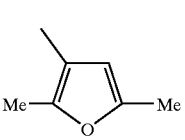 2,5-dimethyl-3-methylfuryl | 177–178 (dec.) |
| 40 | Me | H | Ph | 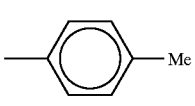 4-Me-C₆H₄ | 163 (dec.) |

EXAMPLE 41

Affinity Determination

The binding of the compounds of the formula I to 5-HT6 receptors was determined as follows:

The substances to be assayed were dissolved in DMSO at a concentration of 1 mM and diluted to the desired concentrations (0.1 nM to 10 µM) with assay buffer (20 mM HEPES, 0.1% ascorbic acid, adjusted to pH 7.4 with NaOH).

20 µl of the respective substance solution were incubated with 80 µl of $^3$H-LSD solution (TRK-1041, Amersham Pharmacia, Freiburg, spec. act. 80–90 Ci/mmol, 1 nM in the mixture) and 100 µl of membrane suspension (5-HT6 receptors, RB-HS6, Biotrend, Cologne, 25–30 µg of protein) at 37° C. for one hour. The reaction mixture was filtered through GFB filters (Whatman) which had been pretreated with 0.1% aqueous polyethyleneimine solution for one hour. The filters were washed three times with 3 ml of assay buffer, transferred into minivials and the radioactivity was determined in a liquid scintillation counter after addition of Ultima Gold (Packard, Frankfurt). The evaluation and IC$_{50}$ determination were carried out using internal programs in RS1 (BBN Software Cooperation).

The compounds of the formula I have a selective affinity for 5-HT6 receptors with an inhibition constant IC$_{50}$ of less than 4 nmol/l.

EXAMPLE 42

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

EXAMPLE 43

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE 44

Solution

A solution of 1 g of an active compound of the formula I, 9.38 g of NaH$_2$PO$_4$.H$_2$O, 28.48 g of Na$_2$HPO$_4$.2H$_2$O and 0.1 g of benzalkonium chloride in 940 ml of double-distilled water is prepared. It is adjusted to pH 6.8, made up to 1 l and sterilized by irradiation. This solution can be used in the form of eye drops.

EXAMPLE 45

Ointment 500 mg of an active compound of the formula I are mixed with 99.5 g of petroleum jelly under aseptic conditions.

EXAMPLE 46

Tablets

A mixture of 1 kg of active compound of the formula I, 4 kg of lactose, 1.2 kg of potato starch, 0.2 g of talc and 0.1 kg of magnesium stearate is compressed to give tablets in a customary manner such that each tablet contains 10 mg of active compound.

EXAMPLE 47

Coated Tablets

Analogously to Example E, tablets are pressed and are then coated in a customary manner with a coating of sucrose, potato starch, talc, tragacanth and colourant.

EXAMPLE 48

Capsules 2 kg of active compound of the formula I are filled into hard gelatin capsules in the customary manner such that each capsule contains 20 mg of the active compound.

EXAMPLE 49

Ampoules

A solution of 1 kg of active compound of the formula I in 60 ml of double-distilled water is sterile-filtered, filled into ampoules, lyophilized under sterile conditions and aseptically sealed. Each ampoule contains 10 mg of active compound.

What is claimed is:

1. A compound of formula (I)

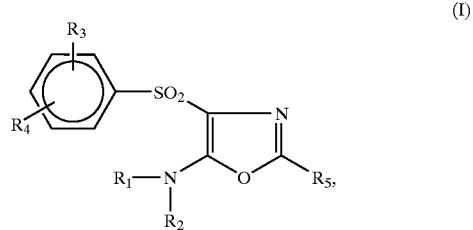

where

R$_1$ and R$_2$ independently of one another are H, —R$_6$, —C$_3$–C$_8$-cycloalkyl, —(CH$_2$)$_n$—R$_7$, —(CH$_2$)$_n$—O—R$_6$, —(CH$_2$)$_n$—NH$_2$, —(CH$_2$)$_n$—NHR$_6$, —(CH$_2$)—N(R$_6$)$_2$, —C$_2$–C$_6$-alkenyl or together form a mononuclear saturated heterocycle wherein said heterocycle is piperazine, R$_3$ and R$_4$ independently of one another are H, —R$_6$, —CF$_3$, —NO$_2$, —Hal, —OH, —O—R$_6$, —NH$_2$, —NH—R$_6$ or —N(R$_6$)$_2$, R$_5$ is a saturated or unsaturated heterocycle wherein said heterocycle is pyridyl which may be mono- or disubstituted by —R$_6$, —CF$_3$, —NO$_2$, —Hal, —OH, —O—R$_6$, —NH$_2$, —NH—R$_6$ or —N(R$_6$)$_2$, and R$_6$ is C$_1$–C$_6$-alkyl, R$_7$ is R$_3$- and/or R$_4$-substituted phenyl, n is 0 to 2, or a physiologically acceptable salt or solvate thereof.

2. The compound according to claim 1, where R$_1$ is H.

3. The compound according to claim 1, where R$_2$ is R$_6$.

4. The compound according to claim 1, where R$_3$ and R$_4$ are H.

5. The compound according to claim 1, where R$_5$ is 3-pyridyl or 4-pyridyl.

6. A method of preparing a medicament comprising mixing a compound according to claim 1 with a pharmaceutically acceptable vehicle or excipient.

7. A method for the treatment of schizophrenia, depression, a pathological anxiety state, epilepsy, amyotrophic lateral scleroses, Huntington's disease, functional gastropathy, bulimia, anorexia nervosa, a migraine, a drug addiction, a sleeping disorder and/or for the treatment of a head or spinal injury, comprising administering to a patient in need thereof a therapeutically effective amount of a compound of claim 1.

8. A pharmaceutical composition comprising at least one compound according to claim 1 or a physiologically acceptable salt or solvate thereof and, a pharmaceutically acceptable carrier.

9. A process for preparing a compound according to formula (I),

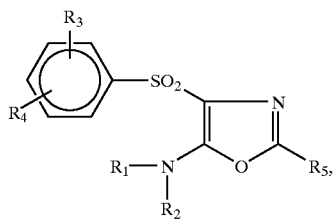

where $R_1$ and $R_2$ independently of one another are H, —$R_6$, —$C_3$–$C_8$-cycloalkyl, —$(CH_2)_n$—$R_7$, —$(CH_2)_n$—O—$R_6$, —$(CH_2)_n$—$NH_2$, —$(CH_2)_n$—$NHR_6$, —$(CH_2)$—N$(R_6)_2$, —$C_2$–$C_6$-alkenyl or together form a mononuclear saturated heterocycle wherein said heterocycle is piperazine, $R_3$ and $R_4$ independently of one another are H, —$R_6$, —$CF_3$, —$NO_2$, —Hal, —OH, —O—$R_6$, —$NH_2$, —NH—$R_6$ or —N$(R_6)_2$, $R_5$ is a saturated or unsaturated heterocycle wherein said heterocycle is pyridyl which may be mono- or disubstituted by —$R_6$, —$CF_3$, —$NO_2$, —Hal, —OH, —O—$R_6$, —$NH_2$, —NH—$R_6$ or —N$(R_6)_2$, and $R_6$ is $C_1$–$C_6$-alkyl, $R_7$ is $R_3$- and/or $R_4$-substituted phenyl, n is 0 to 2, wherein a compound of the general formula (II)

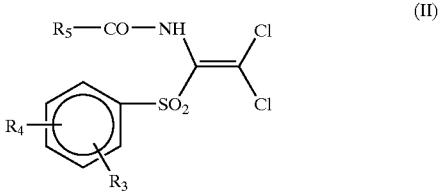

where $R_3$ and $R_4$ independently of one another are H, —$R_6$, —$CF_3$, —$NO_2$, —Hal, —OH, —O—$R_6$, —$NH_2$, —NH—$R_6$ or —N$(R_6)_2$, $R_5$ is a saturated or unsaturated heterocycle wherein said heterocycle is pyridyl which may be mono- or disubstituted by —$R_6$, —$CF_3$, —$NO_2$, —Hal, —OH, —O—$R_6$, —$NH_2$, —NH—$R_6$ or —N$(R_6)_2$, and $R_6$ is $C_1$–$C_6$-alkyl, or (III)

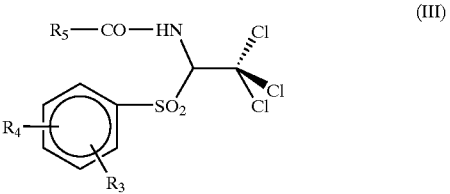

where $R_3$ and $R_4$ independently of one another are H, —$R_6$, —$CF_3$, —$NO_2$, —Hal, —OH, —O—$R_6$, —$NH_2$, —NH—$R_6$ or —N$(R_6)_2$, $R_5$ is a saturated or unsaturated heterocycle wherein said heterocycle is pyridyl which may be mono- or disubstituted by —$R_6$, —$CF_3$, —$NO_2$, —Hal, —OH, —O—$R_6$, —$NH_2$, —NH—$R_6$ or —N$(R_6)_2$, and $R_6$ is $C_1$–$C_6$-alkyl, is reacted with $R_1R_2$NH, wherein $R_1$ and $R_2$ independently of one another are H, —$R_6$, —$C_3$–$C_8$-cycloalkyl, —$(CH_2)_n$—$R_7$, —$(CH_2)_n$—O—$R_6$, —$(CH_2)_n$—$NH_2$, —$(CH_2)_n$—$NHR_6$, —$(CH_2)$—N$(R_6)_2$, —$C_2$–$C_6$-alkenyl or together form a mononuclear saturated heterocycle wherein said heterocycle is piperazine and $R_3$ and $R_4$ independently of one another are H, —$R_6$, —$CF_3$, —$NO_2$, —Hal, —OH, —O—$R_6$, —$NH_2$, —NH—$R_6$ or —N$(R_6)_2$, $R_6$ is $C_1$–$C_6$-alkyl, $R_7$ is $R_3$- and/or $R_4$-substituted phenyl, and n is 0 to 2.

10. The method of claim 6, wherein said medicament is an anticonvulsant, a nootropic, an anti-inflammatory, a neuroprotectant or a cerebroprotectant.

* * * * *